(12) United States Patent
Robert et al.

(10) Patent No.: US 9,220,833 B2
(45) Date of Patent: Dec. 29, 2015

(54) MEDICAMENT INFUSION SYSTEMS

(75) Inventors: Renee Robert, Shoreview, MN (US);
Chad Amborn, Minneapolis, MN (US);
Geoff Clark, Lempster, NH (US)

(73) Assignee: SMITHS MEDICAL ASD, INC.,
Rockland, MA (US)

( * ) Notice: Subject to any disclaimer, the term of this patent is extended or adjusted under 35 U.S.C. 154(b) by 622 days.

(21) Appl. No.: 13/517,782

(22) Filed: Jun. 14, 2012

(65) Prior Publication Data

US 2012/0330238 A1    Dec. 27, 2012

Related U.S. Application Data

(60) Provisional application No. 61/457,879, filed on Jun. 27, 2011.

(51) Int. Cl.
| | | |
|---|---|---|
| *A61M 1/00* | (2006.01) | |
| *A61M 5/00* | (2006.01) | |
| *A61M 5/14* | (2006.01) | |
| *A61M 5/168* | (2006.01) | |
| *A61M 39/10* | (2006.01) | |

(52) U.S. Cl.
CPC . *A61M 5/00* (2013.01); *A61M 5/14* (2013.01);
*A61M 5/168* (2013.01); *A61M 39/1011*
(2013.01); *A61M 2039/1094* (2013.01)

(58) Field of Classification Search
CPC ............... A61M 2039/1094; A61M 39/1011;
A61M 5/00; A61M 5/14; A61M 5/168;
A61M 39/00; A61M 39/10; A61M 2039/1016;
A61M 2039/1027; A61M 2039/1077
USPC ........................................................ 604/151
See application file for complete search history.

(56) References Cited

U.S. PATENT DOCUMENTS

| | | |
|---|---|---|
| 1,871,370 A | 8/1932 | Jacques |
| 3,170,667 A | 2/1965 | Szohatzky |
| 3,287,031 A | 11/1966 | Simmons et al. |

(Continued)

FOREIGN PATENT DOCUMENTS

| | | |
|---|---|---|
| CN | 101212995 A | 7/2008 |
| CN | 101528283 A | 9/2009 |

(Continued)

OTHER PUBLICATIONS

Chinese Office Action issued Apr. 6, 2012 re: CN Appln No. 2011101192607.

(Continued)

*Primary Examiner* — Jason Flick
(74) *Attorney, Agent, or Firm* — Louis Woo

(57) ABSTRACT

A drug delivery system has a fluid store that has a first tubing having an outlet fitted with a connector of a given configuration that prevents the connector from being coupled to a conventional counterpart connector. The system further has a tube retaining device that has a catheter extending out of one of its ends and an inlet connector at its other end that has a configuration complementary to the configuration of the outlet connector of the first tubing, so that the first tubing may be matingly connected to the tube retaining device to establish a through fluid path from the first tubing to the catheter. A one-way valve may be provided to the tubing to prevent fluid from flowing backwards into the tubing. The tubing can be selectively occluded and opened to regulate the flow of fluid from the tubing to the catheter.

20 Claims, 10 Drawing Sheets

(56) References Cited

U.S. PATENT DOCUMENTS

| | | |
|---|---|---|
| 4,076,285 A | 2/1978 | Martinez |
| 4,080,737 A | 3/1978 | Fleer |
| 4,116,476 A | 9/1978 | Porter et al. |
| 4,137,917 A | 2/1979 | Cohen |
| 4,150,673 A | 4/1979 | Watt |
| 4,211,439 A | 7/1980 | Moldestad |
| 4,280,723 A | 7/1981 | Moldestad |
| 4,452,473 A | 6/1984 | Ruschke |
| 4,453,927 A | 6/1984 | Sinko |
| 4,619,640 A | 10/1986 | Potoisky et al. |
| 4,682,981 A | 7/1987 | Suzuki et al. |
| 4,758,225 A | 7/1988 | Cox et al. |
| 4,790,567 A | 12/1988 | Kawano et al. |
| 4,940,458 A | 7/1990 | Cohn |
| 5,069,225 A | 12/1991 | Okamura |
| 5,078,703 A | 1/1992 | Bryant |
| 5,308,335 A | 5/1994 | Ross et al. |
| 5,393,101 A | 2/1995 | Matkovich |
| 5,405,339 A | 4/1995 | Kohnen et al. |
| 5,405,340 A | 4/1995 | Fageol et al. |
| 5,419,770 A | 5/1995 | Crass et al. |
| 5,538,399 A | 7/1996 | Johnson |
| 5,545,152 A | 8/1996 | Funderburk et al. |
| 5,562,121 A | 10/1996 | Hodges et al. |
| 5,591,143 A | 1/1997 | Trombley, III et al. |
| D378,130 S | 2/1997 | Schmidt |
| 5,605,359 A | 2/1997 | Hoff |
| D378,405 S | 3/1997 | Musgrave et al. |
| 5,616,133 A | 4/1997 | Cardenas |
| 5,620,427 A | 4/1997 | Werschmidt et al. |
| 5,632,735 A | 5/1997 | Wyatt et al. |
| 5,651,776 A | 7/1997 | Appling et al. |
| 5,688,254 A | 11/1997 | Lopez et al. |
| 5,695,473 A | 12/1997 | Olsen |
| 5,725,511 A | 3/1998 | Urrutia |
| 5,741,084 A | 4/1998 | Del Rio et al. |
| 5,741,269 A | 4/1998 | McCredy |
| 5,749,861 A | 5/1998 | Guala et al. |
| 5,788,674 A * | 8/1998 | McWilliams .................. 604/141 |
| 5,810,398 A | 9/1998 | Matkovich |
| 5,853,391 A | 12/1998 | Bell |
| 5,855,230 A | 1/1999 | Guala et al. |
| 5,925,028 A | 7/1999 | Delvigo |
| 5,947,937 A | 9/1999 | Urrutia et al. |
| D417,733 S | 12/1999 | Howell et al. |
| D421,119 S | 2/2000 | Musgrave et al. |
| 6,027,480 A | 2/2000 | Davis et al. |
| 6,156,025 A | 12/2000 | Niedospial et al. |
| 6,171,281 B1 | 1/2001 | Zhang |
| 6,197,007 B1 | 3/2001 | Thorne et al. |
| 6,244,632 B1 | 6/2001 | Gasparini |
| 6,309,543 B1 | 10/2001 | Fenton |
| D452,003 S | 12/2001 | Niermann |
| D452,314 S | 12/2001 | Niermann |
| 6,402,207 B1 | 6/2002 | Segal et al. |
| 6,422,607 B1 | 7/2002 | Kirby |
| 6,428,514 B1 | 8/2002 | Goebel et al. |
| 6,475,190 B2 | 11/2002 | Young |
| 6,500,153 B1 | 12/2002 | Sheppard et al. |
| 6,506,181 B2 | 1/2003 | Meng et al. |
| 6,511,472 B1 | 1/2003 | Hayman et al. |
| D469,870 S | 2/2003 | Niermann et al. |
| 6,536,805 B2 | 3/2003 | Matkovich |
| 6,558,353 B2 | 5/2003 | Zohmann |
| 6,612,624 B1 | 9/2003 | Segal et al. |
| 6,656,161 B2 | 12/2003 | Young et al. |
| 6,688,651 B2 | 2/2004 | Min-cheol |
| 6,722,705 B2 | 4/2004 | Korkor |
| 6,786,131 B2 | 9/2004 | Tsai |
| 6,802,836 B2 | 10/2004 | Bouphavichith et al. |
| 6,843,513 B2 | 1/2005 | Guala |
| 6,893,056 B2 | 5/2005 | Guala |
| 6,953,448 B2 | 10/2005 | Moulton et al. |
| 6,988,423 B2 | 1/2006 | Bolam et al. |
| 7,115,228 B2 | 10/2006 | Lundtveit et al. |
| 7,240,927 B2 | 7/2007 | Chang |
| 7,270,349 B2 | 9/2007 | Bamberger et al. |
| 7,641,648 B2 | 1/2010 | Bouphavichith et al. |
| 7,857,805 B2 | 12/2010 | Raines |
| 7,955,315 B2 | 6/2011 | Feinberg et al. |
| 2001/0049490 A1 | 12/2001 | Slanda et al. |
| 2002/0079258 A1 | 6/2002 | Sawa |
| 2003/0105428 A1 | 6/2003 | Hogan et al. |
| 2004/0167474 A1 | 8/2004 | Meng et al. |
| 2004/0201216 A1 | 10/2004 | Segal et al. |
| 2005/0090801 A1 | 4/2005 | Racz et al. |
| 2005/0225082 A1 | 10/2005 | Dalle et al. |
| 2006/0264897 A1 | 11/2006 | Lobl et al. |
| 2007/0270758 A1 | 11/2007 | Hanner et al. |
| 2008/0086094 A1 * | 4/2008 | Peters .......................... 604/246 |
| 2008/0177250 A1 | 7/2008 | Howlett et al. |
| 2008/0287919 A1 | 11/2008 | Kimball |
| 2008/0312640 A1 | 12/2008 | Grant |
| 2009/0099552 A1 | 4/2009 | Levy et al. |
| 2009/0187166 A1 | 7/2009 | Young |
| 2009/0243281 A1 | 10/2009 | Seifert et al. |
| 2009/0299339 A1 | 12/2009 | Young |
| 2009/0312630 A1 | 12/2009 | Hidem et al. |
| 2010/0022951 A1 | 1/2010 | Ferrera et al. |
| 2010/0094260 A1 | 4/2010 | Cude et al. |
| 2013/0289483 A1 * | 10/2013 | Beck et al. .................... 604/151 |

FOREIGN PATENT DOCUMENTS

| | | |
|---|---|---|
| CN | 201324438 Y | 10/2009 |
| CN | 101687091 A | 3/2010 |
| CN | 101756785 A | 6/2010 |
| CN | 102065927 A | 5/2011 |
| EP | 217055 | 4/1987 |
| EP | 774270 | 5/1997 |
| EP | 1010439 | 6/2000 |
| FR | 2642139 | 7/1990 |
| GB | 771967 | 4/1957 |
| JP | H11-319114 | 11/1999 |
| JP | 2001-187990 | 7/2001 |
| WO | 1997-32618 | 9/1997 |
| WO | WO 97/32618 | 9/1997 |
| WO | WO 01/83001 | 11/2001 |
| WO | WO 2004/037335 | 5/2004 |
| WO | 2005/044335 | 10/2004 |
| WO | 2006-125789 | 11/2006 |
| WO | WO 2007/030403 | 3/2007 |

OTHER PUBLICATIONS

Canadian Office Action issued Apr. 13, 2012 re: CA Appln No. 2575136.

Sheppard et al., "Improving patient safety by design—a new spinal/intrathecal injection safety system", Can J Anesth 2006; 0108-9.

Chinese Search Report, dated May 18, 2015, re: co-pending Chinese Patent Application No. 201280042020.4 (with English translation).

European Search Report, dated Jul. 7, 2015, co-pending European Patent Application No. 12803701.7.

* cited by examiner

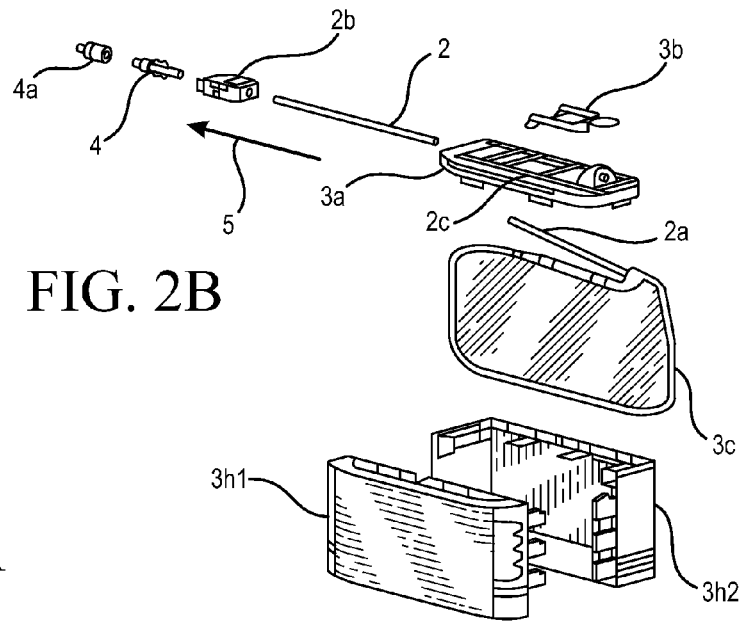
FIG. 2B
FIG. 2A
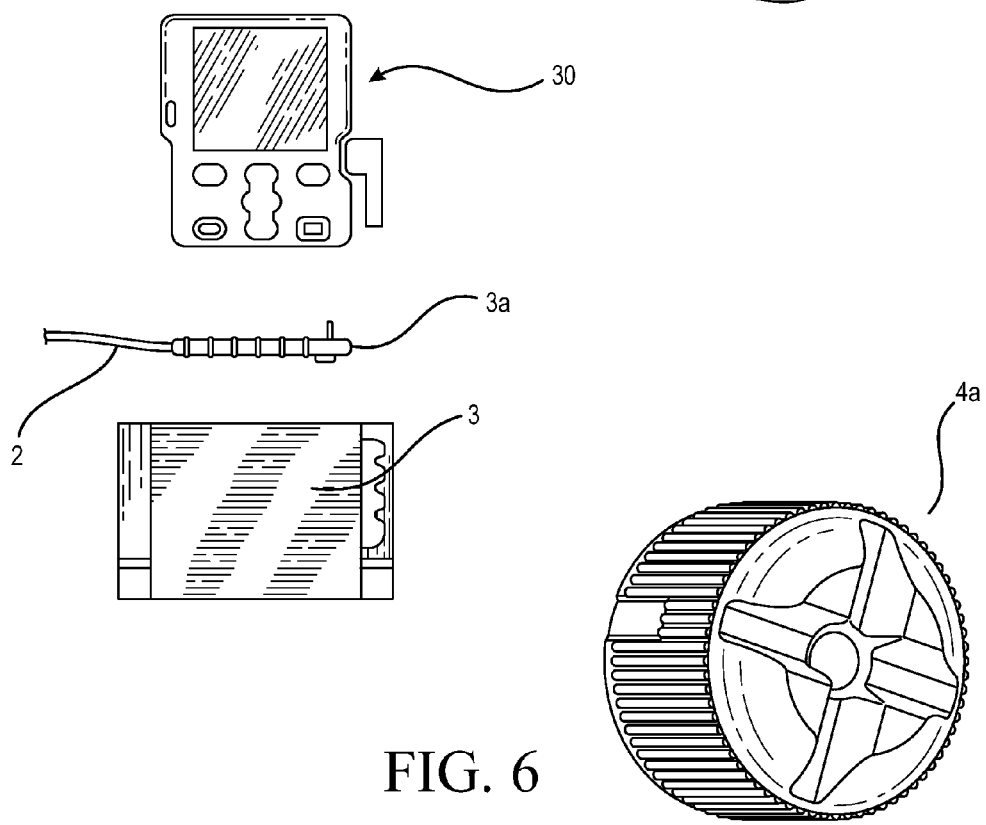
FIG. 6

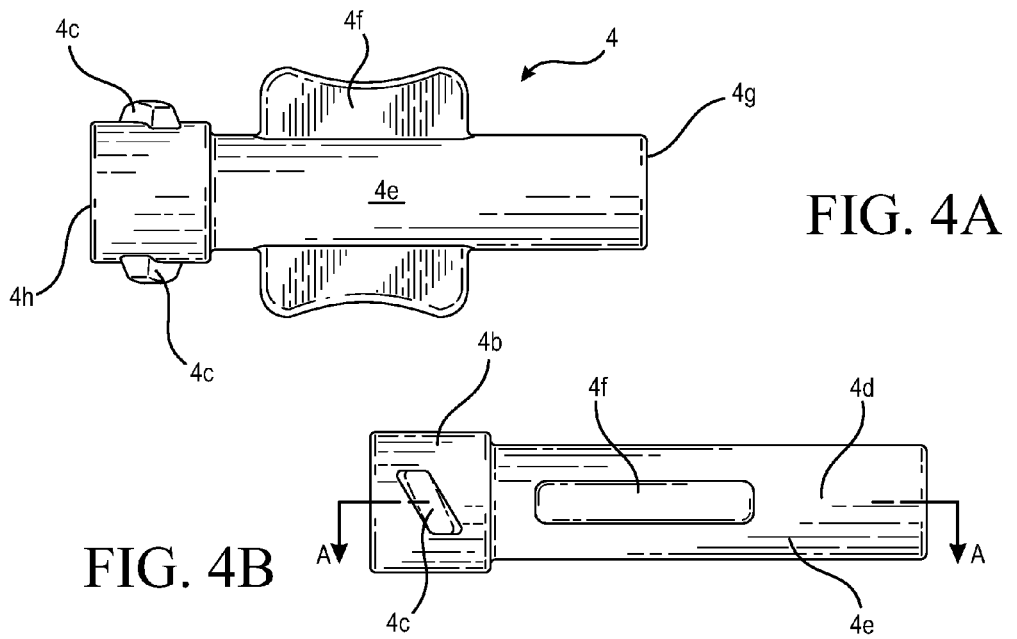
FIG. 4A
FIG. 4B
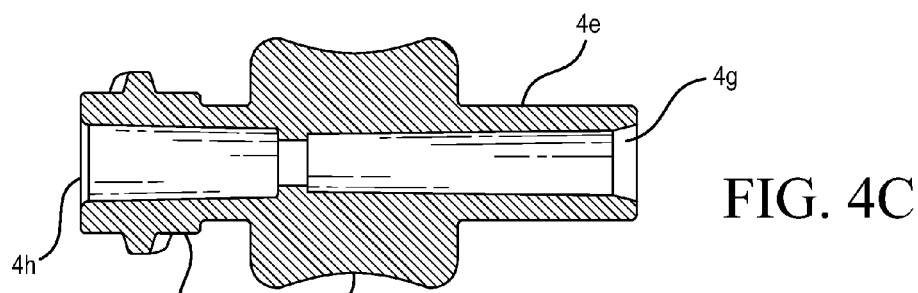
FIG. 4C
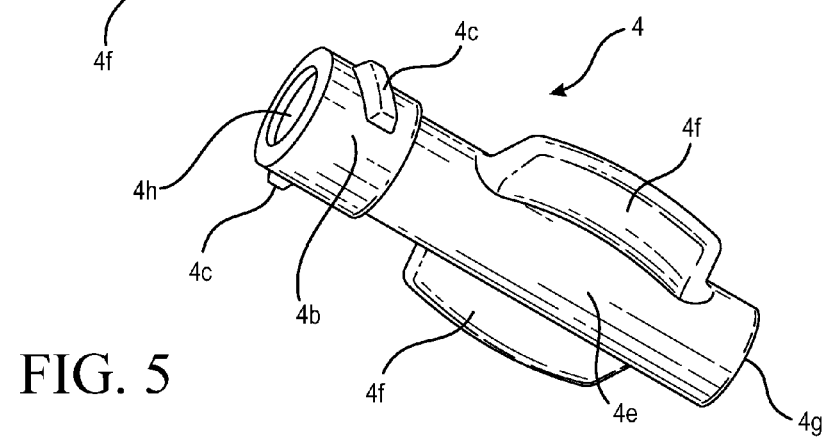
FIG. 5

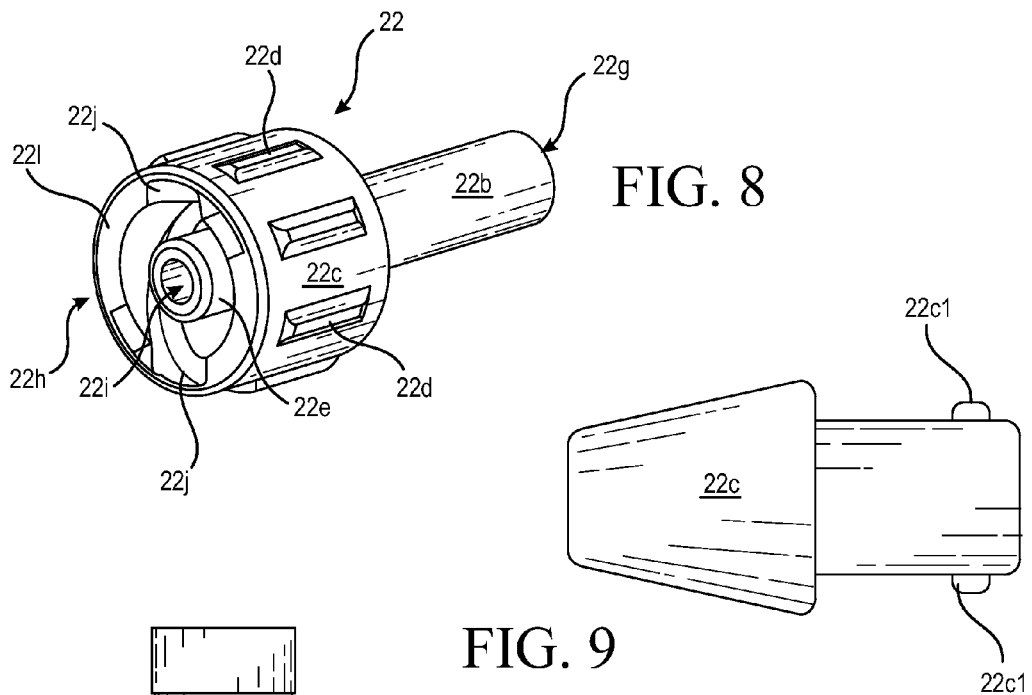
FIG. 8
FIG. 9
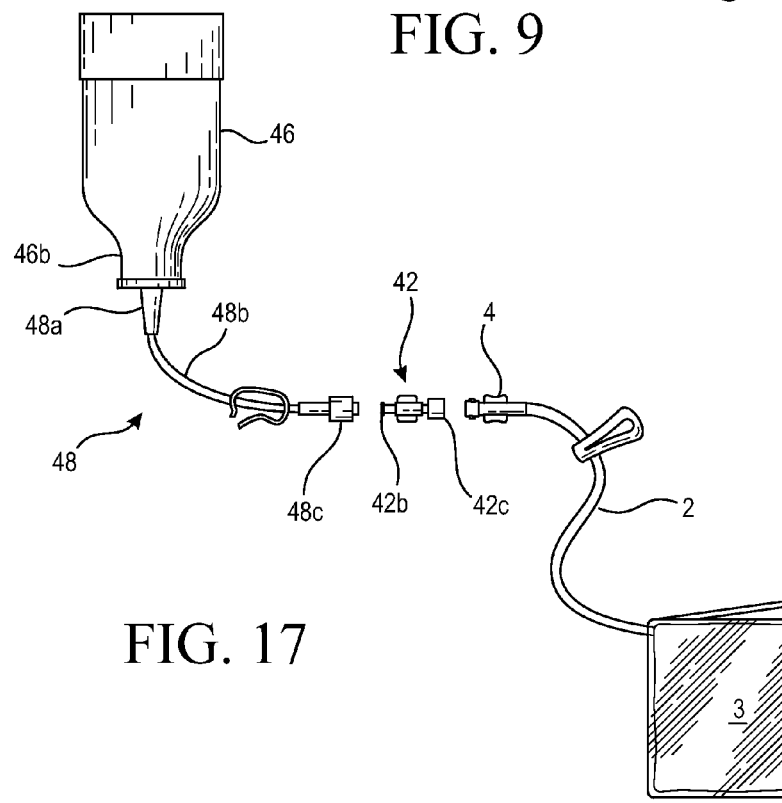
FIG. 17

MEDICAMENT INFUSION SYSTEMS

FIELD OF THE INVENTION

The present invention relates to medicament infusion systems and more particularly to an ambulatory infusion system that has specially designed connectors that prevent the inadvertent connection of the system to the wrong medicament for infusion to a patient.

BACKGROUND OF THE INVENTION

Medicament infusion systems are known. Some of these systems include the use of medical infusion pumps that are portable or ambulatory so as to allow a patient to maintain his daily activities while at the same time continue to receive the intravenous infusion being administered by a medical infusion pump. Such medical infusion pumps include those sold by the assignee of the instant invention under the trade names CADD™ Prizm, CADD™ Legacy, and CADD™ Solis. Those pumps each require that there be a number of conduits connected to each other so that the medicament stored in a fluid store such as a cassette may be fed through various routes of delivery to the patient including for example intravenously or neuraxially.

Given that there are different types of medications each directed to a given ailment or procedure, and further that the connectors of the various conduits are manufactured to have a standard or conventional configuration, the possibility exists that the wrong medicament may be provided to the patient due to mistaken connection of the wrong conduits. For example, if the medicament to be used for chemotherapy were to be infused to a patient as an epidural medication, grave harm may be caused to the patient.

There is therefore a need for a medicament infusion system where the different conduits, tubings and/or catheters of the system cannot be mistakenly connected so that infusion of the wrong medicament to the patient is prevented.

SUMMARY OF THE PRESENT INVENTION

The drug delivery system of the instant invention is a specialty connection system designed to minimize the risk of medication administration errors and is designed to replace the standard or conventional connectors such as luer connectors that are currently being utilized with their respective conduits to convey, among other medicament products, epidural and spinal anesthesia medicaments. The connectors for the various conduits of the drug delivery system of the instant invention are designed such that they are incompatible with the standard or conventional connectors such as luer connectors that are manufactured in accordance with the ISO (International Standard Organization) Standards 594-1 and 594-2, but are compatible only with specially designed counterpart complementary connectors. Thus, a female/male connector of the drug delivery system of the instant invention is compatible with and matable only to a counterpart complementary male/female connector, while incompatible with the conventional or standard connectors that are made under the aforementioned ISO standards.

A first embodiment of the instant invention drug delivery system includes a first tubing that has an insert that may be in the shape of a hollow spike used to pierce a fluid store such as a plastics medicament storage bag that stores the appropriate medicament for the patient. The first tubing has at its outlet a first connector of a given configuration that prevents the connector from being mated with a counterpart connector of a conventional configuration. The outlet connector of the tubing may be either a male or female connector, but for the exemplar first embodiment being discussed is a male connector of the given configuration. A tube retainer or connection device to which a second tubing is retained has an inlet connector that has a configuration complementary to the given configuration of the outlet connector of the first tubing, so that the inlet connector of the tube retainer device is only connectable to the outlet connector of the first tubing and not to a counterpart connector that has a conventional configuration. Once the outlet connector of the first tubing and the inlet connector of the tube device are matedly coupled to each other, a fluid communication path is established between the first tubing and the second tubing so that fluid or medicament from the fluid store may be conveyed to the second tubing.

The second tubing may be a catheter having one end non-occludedly retained by the tube retainer device and its other end inserted to the patient for neuraxially infusing the medicament to the patient. To prevent back flow of the medicament or infusate from the second tubing to the first tubing, a one-way flow valve is bonded to or integrated to the outlet connector of the first tubing to ensure that the medicament only flows unidirectionally from the fluid store to the patient.

The drug delivery system further includes a mounting or support press plate onto which a portion of the first or second tubing, preferably the first tubing, may be positioned or mounted thereon. The mounting plate may be coupled to a computerized ambulatory infusion pump, so that the expulsor and valves associated with the infusion pump would act or selectively press on that portion of the tubing to selectively occlude and open the tubing to thereby regulate the flow and the amount of the medicament from the fluid store to be infused to the patient.

In a second embodiment of the instant invention, the fluid store may be considered to be a part of a cassette attached to the mounting plate that couples to the computerized infusion pump. The cassette houses a bag made from medical plastics into which the medicament is stored. A first tubing has an inlet that extends from the bag and is therefore in fluid communication with the medicament storage bag. A portion of the first tubing extending from the bag outside of the cassette is positioned onto the mounting plate, which may be coupled to a computerized infusion pump so that, as was the case in the first embodiment, the flow and the amount of medicament output from the storage cassette may be regulated. The second embodiment may also have a tube retainer device as described above in the first embodiment. But for this embodiment, the output connector of the first tubing from the fluid storage cassette and the inlet connector of the tube retainer device are of the same type, i.e., a female connector of a given configuration that prevents it from being connected to a counterpart male connector of a conventional configuration.

For the second embodiment there is an extension tubing that has a first end and a second end fitted with a third connector and a fourth connector, respectively. Each of the third and fourth connectors has a configuration that is complementary to the given configuration of the first tubing and the tube retainer connectors, so that the third and fourth connectors are counterpart connectors to the output connector of the first tubing and the inlet connector of the tube retainer device. When interposedly connected to the first tubing and the tube retainer device, the extension tubing provides a conduit between the first tubing and the tube retainer device to establish a through path where fluid flows from the fluid store bag to the patient. The fluid stored in the fluid store bag may be for example epidural medicament.

The present invention is therefore directed to a drug delivery system that comprises a fluid store for storing a medicament, a first tubing having an inlet in fluid communication with the fluid store so that the medicament flows from the fluid store through the first tubing. The first tubing has an outlet first connector of a given configuration that prevents the outlet first connector from mating with a counterpart connector having a conventional configuration. The drug delivery system further includes a tube retainer device that has a second tubing coupled thereto for interfacing with a patient that includes an inlet second connector having a configuration complementary to the given configuration of the outlet first connector of the first tubing, so that the inlet second connector is connectable only to the outlet first connector and not to a counterpart connector having a conventional configuration. A one-way flow valve may be integrated to the outlet first connector to prevent back flow of the medicament from the second tubing to the first tubing, when the outlet first connector and the inlet second connector of complementary given configurations are connected to a each other.

A second embodiment of the drug delivery system of the instant invention comprises a fluid store for storing a medicament, a first tubing that has an inlet connected to the fluid store and an outlet first connector of a given configuration that prevents the outlet first connector from connecting with a counterpart connector of a conventional configuration, a tube retainer device that has a second tubing and an inlet second connector that has the same given configuration as the outlet first connector of the first tubing so that the inlet second connector is also not connectable to a counterpart connector of a conventional configuration, and an extension tubing having a first end fitted with a third connector and a second end fitted with a fourth connector each having a configuration that is complementary to the given configuration of the first and second connectors so that the third connector is connectable to the first connector and the fourth connector is connectable to the second connector to establish a fluid through path between the fluid store and the second tubing.

The present invention is also directed to a drug delivery system that has a fluid store that stores a medicament, a first tubing having an inlet in fluid communication connection with the fluid store and an outlet female connector of a given configuration that prevents it from mating with a counterpart male connector of a conventional configuration, a tube retainer device having a catheter and an inlet female connector that has the same configuration as the outlet female connector of the first tubing, and an extension tubing having a first end male connector and a second end male connector each having a configuration complementary to the given configuration of the outlet female connector of the first tubing and the inlet female connector of the tube retainer device, so that the first and second end male connectors can be respectively connected to the outlet female connector of the first tubing and the inlet female connector of the tube retainer device to establish a fluid path from the fluid store to the catheter.

The present invention is further directed to a drug delivery system that has a fluid store that stores a medicament, a first tubing having an inlet in fluid communication with the fluid store and an outlet male connector of a given configuration that prevents it from mating with a female connector of a conventional configuration, and a tube retainer device that has a second tubing and an inlet female connector having a complementary configuration to the given configuration of the outlet male connector of the first tubing so that the inlet female connector is connectable only to the outlet male connector of the first tubing to thereby establish a through path for the medicament to flow from the fluid store to the patient through the first and second tubings when the outlet male connector and the inlet female connector are connected to each other, and a mount whereonto a portion of the first tubing is positioned, so that a flow control mechanism of a computerized control pump coupled to the mount can interact with the first tubing to selective occlude and open the first tubing to regulate the flow and the amount of medicament to be dispensed to the patient.

The present invention is furthermore directed to a fitting for establishing a fluid through path between a first connector of a conventional configuration and a second connector of a given configuration not matable with the first connector. The fitting has a body having a first end connector with a counterpart conventional configuration that is matable to the first connector and a second end connector with a counterpart given configuration that is matable to the second connector. The body further has a through passage so that a fluid through path is established between the first and second connectors when the first end connector of the fitting is matingly coupled to the first connector and the second end connector of the fitting is matingly coupled to the second connector. With the fitting of the instant invention, medicament may be transferred from an IV bottle with a conventional set having a conventional luer connector or a syringe with a conventional luer connector to the cassette or other fluid store of the medicament infusion system of the instant invention.

BRIEF DESCRIPTION OF THE FIGURES

The instant invention will best be understood with reference to the following drawings, wherein:

FIG. 2a shows a computerized ambulatory drug delivery (CADD) infusion pump and the fluid store cassette that couples to the pump;

FIG. 2b is an exploded view of the cassette, the mounting or press plate of the cassette and the tubing in fluid communication with the plastic storage bag inside the cassette that has a portion thereof mounted onto the press plate;

FIG. 4a is a top view of the female connector of the instant invention that has a given configuration;

FIG. 4b is a side view of the female connector of FIG. 4a;

FIG. 4c is a cross-sectional view of the female connector of FIG. 4a;

FIG. 5 is a perspective view of the female connector of the instant invention;

FIG. 6 is a cap for covering the female connector of the instant invention;

FIG. 8 is a perspective view of the male connector of the instant invention;

FIG. 9 is a cap for covering the outlet of the male connector of FIG. 8;

FIG. 11b is a plan view of the outer shells of the clam shell structure of the retainer device of FIG. 11a;

FIG. 17 shows the fitting of FIG. 15 being used to connect an IV bottle to the fluid storage cassette of the instant invention system.

DETAILED DESCRIPTION OF THE INVENTION

Figure 1:
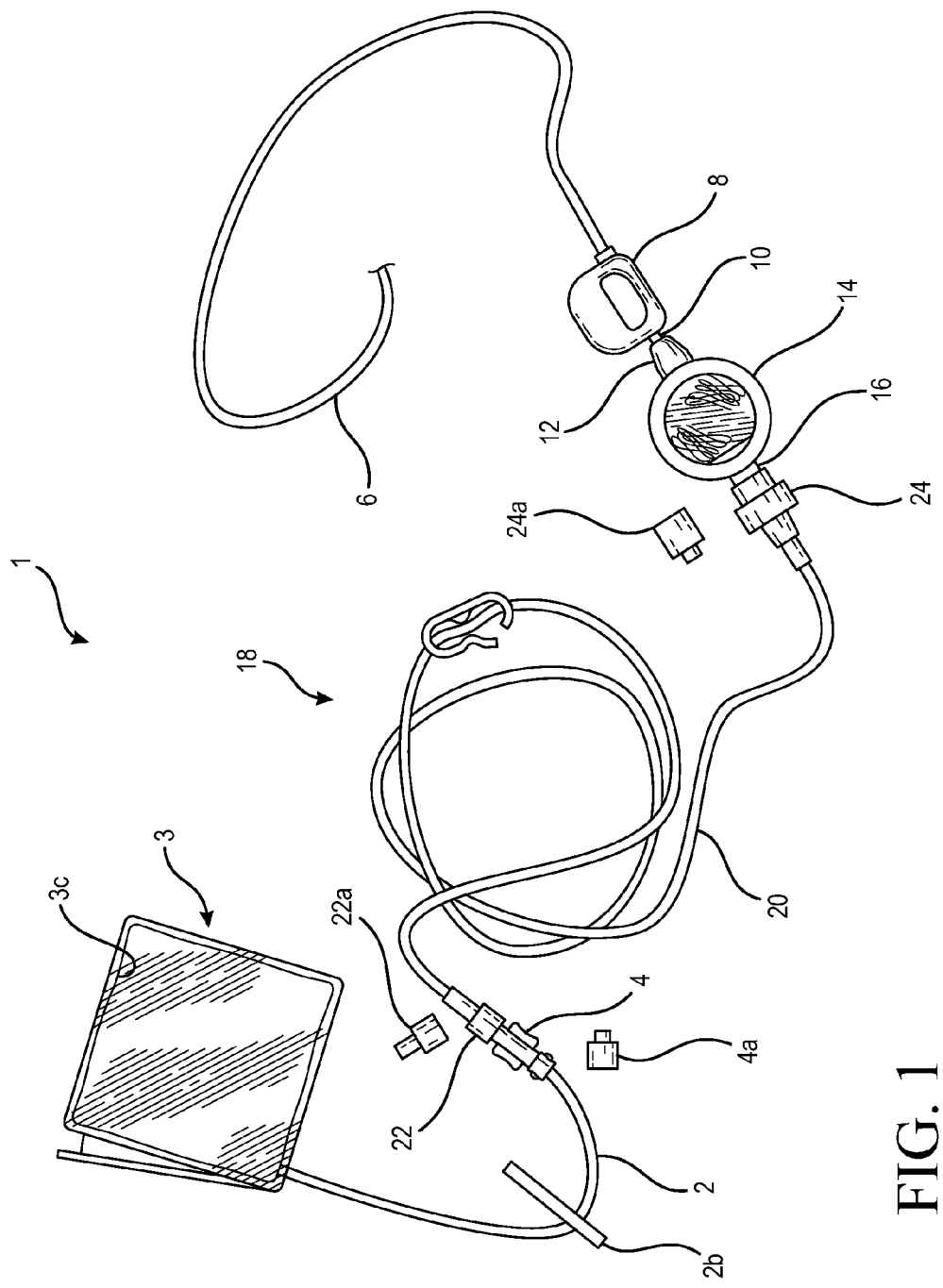
FIG. 1 is an overall view of a first embodiment of the drug delivery system of the instant invention.

An overview of the computerized ambulatory drug delivery (CADD) system of the instant invention is illustrated in FIG. 1. As shown, the drug delivery system 1 of the instant invention includes a fluid line or tubing 2 connected to a fluid store represented by medicament storage cassette 3, more concisely the fluid reservoir or plastics fluid storage bag 3c housed inside the cassette 3. Tubing 2 may be an extension of and is in a fluid communicative manner with bag 3c so that the fluid medicament stored in the cassette can flow from the cassette to the tubing 2. System 1 further includes a catheter 6 that interfaces with or is to be inserted to a patient during a procedure such as for example an epidural whereby the catheter 6 is inserted to the spinal area of the patient with an epidural needle, which is subsequently removed. Catheter 6 is shown to be connected to a tube retainer device 8 that, when in its closed position per shown in FIG. 1, non-occludedly retains catheter 6 by grasping a portion thereof.

Figure 11A:
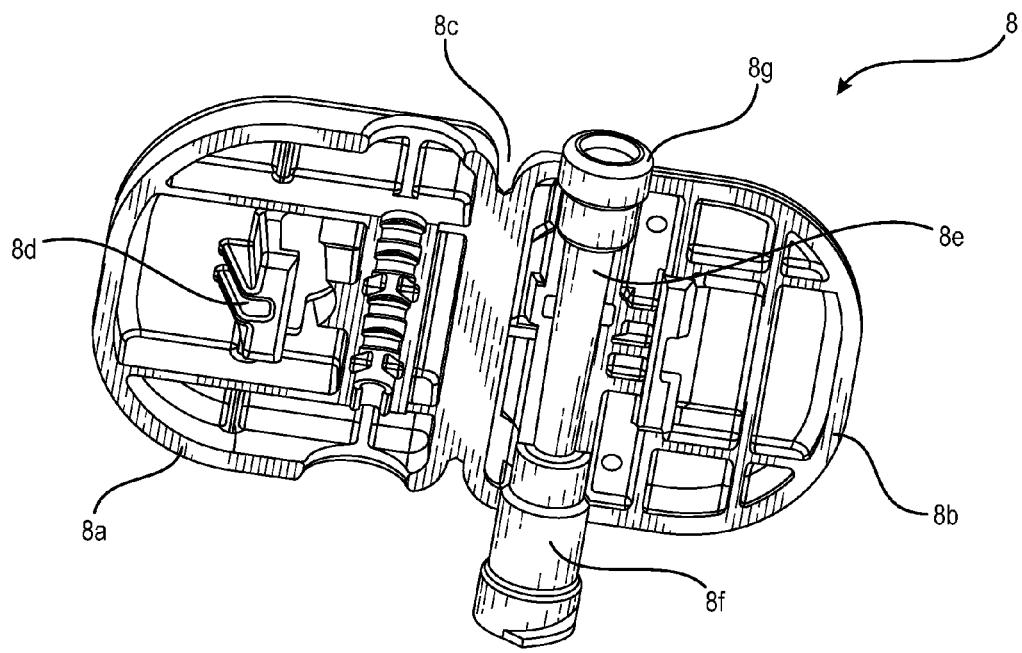
FIG. 11a is a plan view that shows the inner surfaces of the clam shell tube retainer device that may be a part of the drug delivery system of the instant invention.
Figure 11B:
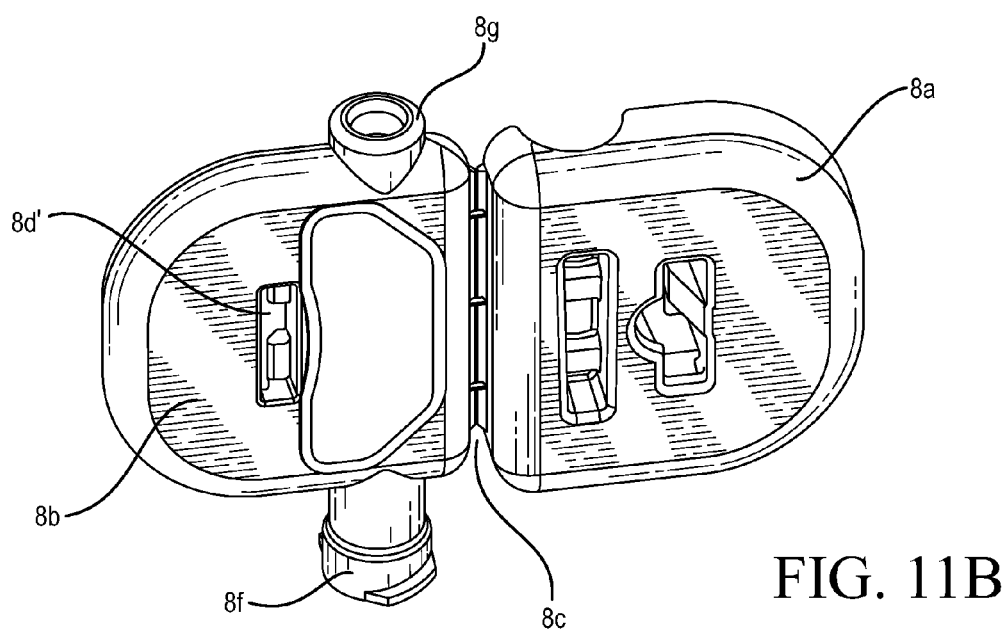

Additional views of the retainer device 8 can be gleaned from FIGS. 11a and 11b, which show the retainer device 8 to be a clamshell like structure having two clamshell members 8a and 8b integrally connected by a living hinge 8c, so that clamshell members 8a and 8b are closeable upon each other. A locking finger structure 8d at member 8a interacts with a coacting locking mechanism 8d' to maintain members 8a and 8b together when members 8a and 8b are pivoted along living hinge 8c to close upon each other. A tube guide 8e made of elastic rubber or plastics material extends along the inside surface of member 8b to be in communication with an inlet connector 8f and an outlet 8g. The configuration of inlet connector 8f is of a given dimension so that it is only matable with a counterpart outlet connector having the complement configuration of the given dimension, and therefore not matable with a counterpart connector of a conventional configuration, as will be discussed infra.

A catheter such as catheter 6 shown in FIG. 1 has its non-patient end insertable into tube retainer device 8 via outlet 8g so as to extend through tube guide 8e and be in fluid communication with the inlet of the inlet connector 8f of the tube retainer device 8. With the non-patient end portion of the catheter being enveloped by tube guide 8e, the catheter is fixedly but non-occludedly retained by the tube retainer device 8 when the device is in its closed position per shown in FIG. 1. A more detailed discussion of the tube retainer device per shown in FIGS. 11a and 11b is given in co-pending application Ser. No. 12/659,020 filed on Feb. 23, 2010 and assigned to the assignee of the instant application. The disclosure of the '020 application is incorporated by reference herein.

Return to FIG. 1. The drug delivery system 1 of the instant invention may further include a filter 14 that has a male connector 12 connected to a counterpart female connector 10 of the tube retainer device 8. At the inlet of filter 14 there is a female connector 16 that may be matingly coupled to a male connector 24 of an extension tubing set 18 that includes an extension tubing 20. Another male connector 22 at the other end of the tubing 20 is matingly connected to a female connector 4 of tubing 2 that extends from cassette 3. Further shown in the overall view of the first embodiment of the instant invention of FIG. 1 are a cap 4a for covering connector 4, and a cap 22a for covering connector 22. There is moreover a shroud cap 24a that covers the male connector 24 of tubing 20. The connectors of the drug delivery system of the instant invention may also be referred to as CORRECTINJECT® (CI) connectors.

FIG. 2a is an illustration of an exemplar computerized ambulatory infusion pump 30 that is representative of the CADD-Solis Ambulatory Infusion Pump being marketed by the assignee of the instant invention. Cassette 3, as shown in FIG. 2a and the exploded view of FIG. 2b, has a mount, or more accurately a mounting or support press plate 3a whereonto a portion of tubing 2, designed 2a, is mounted or positioned onto. A clip 3b is used to maintain a spring action member (not shown) that acts on tube portion 2a to prevent the tube from being crimped when cassette 3 is not coupled to pump 30. The operation of an exemplar drive mechanism, which includes an expulsor and valves, of pump 30 for acting on tube portion 2a to selectively occlude and open tubing 2 to respectively prevent and enable the flow of fluid therethrough, as well as the operation of the pump itself, may be gleaned from U.S. Pat. No. 5,695,473, assigned to the assignee of the instant application. The disclosure of the '473 patent is incorporated by reference herein.

As further shown in FIG. 2b, cassette 3 is made up of two half housing 3h1 and 3h2 that hold an elastic storage bag 3c made of medical plastics that is connected to tubing 2 by means of tubing portion 2a. Tubing 2 may also be an integral extension of fluid store bag 3c so that tubing 2 and the fluid store bag 3c are in fluid communication with each other. Tubing portion 2a, as discussed above, is mounted to or positioned onto press or mounting plate 3a. Tubing portion 2a is shown to be detached from tubing 2 in FIG. 2b for the sake of clarity, but in fact tubing 2 and tubing portion 2a are one continuous tubing. The longitudinal axis along plate 3a whereon portion 2a is positioned is designated 2c. Plate 3a has an opening through which portion 2a passes from its underside. When assembled as shown in FIG. 2a, cassette 3 is coupled to pump 30 by means of mounting plate 3a. A driving mechanism comprising an expulsor and a plurality of valves (not shown in FIG. 2a but described in the afore-noted '473 patent) extending from the bottom of pump 30 come into contact with and selectively press different sections of tubing portion 2a to selectively occlude and open the tubing 2 to thereby control the flow and the amount of flow for the medicament stored in fluid store bag 3c to flow through tubing 2, so that the medicament can be selectively and controllably conveyed through tubing 2 in the direction of arrow 5.

Also shown in FIG. 2b is a crimping clip 2b that is slidable along tubing 2, and may be manipulated by the user to crimp tubing 2 to prevent fluid from passing therethrough. A connector 4 of a given configuration bondedly connected to the distal end of tubing 2, and the cap 4a for covering the connector 4, are also shown in FIG. 2b.

Figure 3:
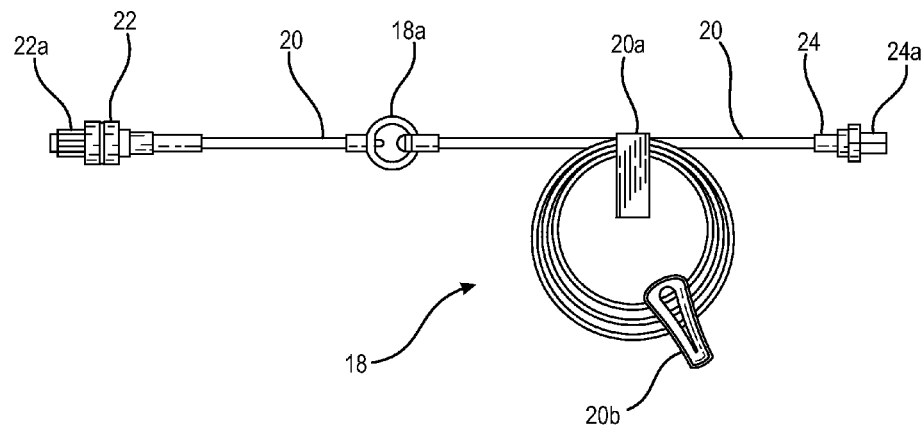
FIG. 3 is an illustration of an exemplar extension tubing set.

FIG. 3 shows an exemplar extension tubing set 18 that is similar to the extension set 18 shown in FIG. 1. The extension set 18 shown in FIG. 3 is slightly different from that shown in FIG. 1 insofar as it includes a filter 18a that is integrated to tubing 20 for filtering any unwanted particulates that may flow along tubing 20. Also shown is a holder 20a that allows the tubing 20 to be coiled for both ease of storage and transport. Further shown as a non-essential portion of extension set 18 is a clip 20b which may be used to crimp or occlude tubing 20 to prevent passage of fluid therealong. At each end of tubing 20 there is bondedly fitted a connector, which for the exemplar tubing 20 is a male connector that has a configuration complementary to the configuration of the female connector 4 of tubing 2 and the female connector 16 of filter 14 shown in FIG. 1. To conform with the designation of the extension set shown in FIG. 1, the male connectors of the FIG. 3 extension set are labeled 22 and 24. Male connectors 22 and 24 are covered by corresponding shroud caps 22a and 24a.

As discussed above, for the drug delivery system 1 of the instant invention shown in FIG. 1, the output of tubing 2 is fitted with a female connector 4 while the tube retainer device 8 to which catheter 6 is attached has a female connector 10 at its end away from the patient. A detailed description of the tube retainer holder 18 may be gleaned from the above-noted co-pending U.S. application Ser. No. 12/659,020 which disclosure is incorporated by reference to the disclosure of this application.

The female connector 10 of the tube retainer device 8 has a given or particular dimension(s), feature(s) and/or configuration that allows it to be connected to a counterpart connector such as male connector 12 that has a complementary dimension(s), feature(s) and/or configuration to connector 10. Connector 12 may be an integral extension of or bondedly fitted to the non-catheter end of the filter 14. Thus, male connector 12 and female connector 10 have complementary features, dimensions and/or configurations that allow those connectors to matingly coupled, connected or fitted to each other, but not with standard connectors such as luer connectors that have conventional configurations manufactured in accordance with ISO (International Standard Organization) Standards 591-1 and 594-2. For ease of discussion, henceforth it should be assumed that the term "configuration" is inclusive of the dimensions and other features of the being discussed connectors that either enable or prevent those connectors and their counterparts (male and female) from matingly connect or couple to each other.

Filter 14 has at its other end a female connector 16 that has the same configuration as female connector 10 so that it too is connectable only to a counterpart male connector that has a configuration that is complementary to the given or special configuration of the female connector 16.

A fluid communication path is established between female connector 4 of tubing 2 and female connector 16 of filter 14 when male connectors 22 and 24 of extension tubing 20 matingly couple to female connectors 4 and 16, respectively. When the drug delivery system shown in FIG. 1 is fully assembled, the medicament from the fluid bag 3c within cassette 3 may be conveyed from tubing 2 to tubing 20, and from there through filter 14 to catheter 6 and then the patient to whom catheter 6 is inserted. A fluid through path is thus established to enable the medicament in the fluid store to be infused to the patient. As the female connectors (4, 16, 10) are only connectable with their counterpart complementary male connectors (22, 24, 12), the drug delivery system of the instant invention ensures that there is no mis-connection of the inventive male and female connectors with conventional connectors.

The top, side and cross-sectional views of the exemplar female connector of the drug delivery system of the instant invention are shown in FIGS. 4A, 4B and 4C, respectively. As all female connectors of the drug delivery system of the instant invention have the same configuration, discussion of the female connector of the instant invention is with reference only to the outlet female connector 4 of tubing 2. As shown, connector 4 has a main body 4e, a connector fitting or end 4b and a tubing end 4g. The tubing end 4g of the connector 4 is for connecting, by solvent or ultrasonic bonding, with a tubing, for example tubing 2 for the connector being discussed. At the connector end 4b of female connector 4 there are two protuberances, or tabs 4c. Tabs 4c, shown to be offset from the longitudinal axis 4d of the female CI connector, are used to threadingly mate connector end 4b to a complementary configured male connector, to be discussed with reference to FIGS. 7A-7D, infra. Two wings 4f extending from body 4e provide the user with a firmer grip of the connector for easier rotational manipulation thereof during use.

With further reference to FIGS. 4A to 4C, an exemplar dimensional feature that merits mention for the inventive connectors is that the opening 4h of the inventive female connector 4 (and the corresponding cone insert for the counterpart male connector to be discussed infra) has been configured with a taper from approximately 4% to 6%, preferably approximately 5% or 3° (3 degrees), as compared to a taper of 6% or 3.44° for the conventional luer female connectors manufactured under the afore-noted ISO standards. As a result, a conventional male luer connector produced in accordance with the afore-noted ISO standards that otherwise mates readily with a conventional female luer connector could not mate with the inventive female connector, as the configuration of the conventional male luer connector is not complementary to the configuration of the inventive female connector. This is due to the opening 4h and the passage tapering therefrom at connector fitting 4b being configured not to accept the fitting of a conventional male connector such as a luer connector. There may be other configurations, for example the orientation of tabs 4c and the width of the mouth of opening 4h, for the inventive female connector in FIGS. 4A-4C, that provide additional features that prevent the inventive female connector to mate with a male connector of a conventional configuration.

The dimensions of the fittings of the male and female connectors of the instant invention are also different from the dimensions of the conventional connectors. For example, the male fitting of a conventional connector such as a luer connector manufactured in accordance with the afore-noted ISO standards has a tip that has a cross section of 3.925 mm at minimum and 4.027 mm at maximum; while the tip of the fitting of a conventional female luer connector has a cross section of 4.270 mm at minimum and 4.315 mm at maximum. The respective fittings for the male and female connectors of the instant invention are configured to have dimensions that are different from the dimensions noted above so that the fittings of the inventive connectors cannot mate with the fittings of counterpart conventional connectors due to the incompatibility of their fittings. For example, the tip of the fitting of the inventive female connector may have a cross section that is smaller than 3.925 mm while the tip of the fitting of the inventive male may have a cross section that is smaller than 4.270 mm, so that the respective fittings of the conventional male/female connectors are not fittable to the fittings of the inventive female/male connectors. A perspective view of the inventive female connector 4 of the instant invention is shown in FIG. 5. The cap 4*a* that has a configuration complementary to connector end 4*b* for covering connector 4 prior to use (or when not in use) is shown in FIG. 6.

The male connector of the drug delivery system of the instant invention is shown in FIGS. 7A-7D. The shown inventive male connector corresponds to male connector 22 shown in FIG. 1. Accordingly, connector 22 will be used for the discussion herein insofar as all the inventive male connectors of the drug delivery system of the instant invention have the same configuration that is complementary to that of the inventive female connector 4 discussed supra, and are therefore matable with the inventive female connector illustrated in FIGS. 4A-4C. Same as the counterpart inventive female connectors, the configuration of the inventive male connectors of the inventive drug delivery system makes those male connectors not matable with counterpart female connectors of a conventional configuration manufactured in accordance with the above discussed ISO standards.

As illustrated in FIGS. 7A-7D, male connector 22 may have a connector stem 22*b* that extends to a connector fitting or mating portion 22*c* having a number of ribs 22*d* that assist the user in grasping and rotating the connector. As best shown in the frontal view of FIG. 7C and the cross-sectional view of FIG. 7B, a cone portion 22*e* extends from the base 22*f* of mating portion 22*c* to establish a through passage 22*i* from the proximal end 22*g* to the tip or distal end 22*h* of the connector. Cone 22*e* is spatially surrounded by a circumferential wall 22I that forms the outer circumferential wall of mating portion 22*c*. Two channels 22*j* notched out of wall 22*l* provide the entrance to the internal thread 22*k* formed at the interior circumferential surface of wall 22*l*. Channels 22*j* and mating portion 22*c* form a configuration that is complementary to the protrusions 4*c* at the connector mating portion 4*b* of the female connector 4, so that the male connector 22 and the female connector 4 may be threadedly mated to each other by means of their respective mating portions 22*c* and 4*b*.

With reference to FIGS. 7A-7D, the exemplar male connector 22 is shown to have a cone portion 22*e* that has a taper from approximately 4% to 6%, preferably 5% or 3° outwards complement to that of the approximately 5% or 3° inward taper of the counter exemplar female connector 4 discussed above. Also, the outer circumferential wall of cone 22*e* has a width that is slightly smaller than the width for the inner circumferential surface of mating portion 4*b* of the female connector 4, so that cone 22*e* can readily fit into the mating portion 4*b* of the female connector 4. The respective widths of the circumferential wall of cone 22*e* and the inner circumferential surface of mating portion 4*b* of the female connector 4 of the instant invention may be dimensioned to be different from (preferably smaller than but could be greater than) those widths or cross sections of the conventional connectors noted above so as to act as another feature that prevents the inventive connectors from being mated to counterpart connectors of conventional configurations. Further, the respective pitches for the tabs 4*c* of the female connector 4 and the internal threads 22*k* of the mating portion 22*c* of the male connector 22 are designed to enable the male connector 22 and the female connector 4 to fittingly mate with each other but prevent either one of those connectors to mate with a counterpart connector having a conventional configuration designed in accordance to the afore-noted ISO standards. A perspective view of the male connector 22 is shown in FIG. 8.

A perspective view of the shroud cap 22*a* that matingly fits to mating portion 22*c* to maintain sterility of the connector is shown in FIG. 9. Note that cap 22*c* also has two protrusions 22*c*1 that threadedly mate to the channels 22*j* of mating portion 22*c* of the connector 22. Although not shown in detail, cap 4*a* for the female connector 4 has a similar cone and internally threaded configuration as the male connector 22. Accordingly, cap 4*a* may be threadingly mated to female CI connector 4 before and possibly after the latter's use. A small air hole (not clearly shown in FIG. 1) may be provided at the tip of cone 4*a* to allow gases such as EtO (Ethylene oxide) to pass through to the cassette to sterilize the cassette. The cap used after the cassette has been filled, for example by a pharmacist, is a non-vented cap.

Figure 10B:
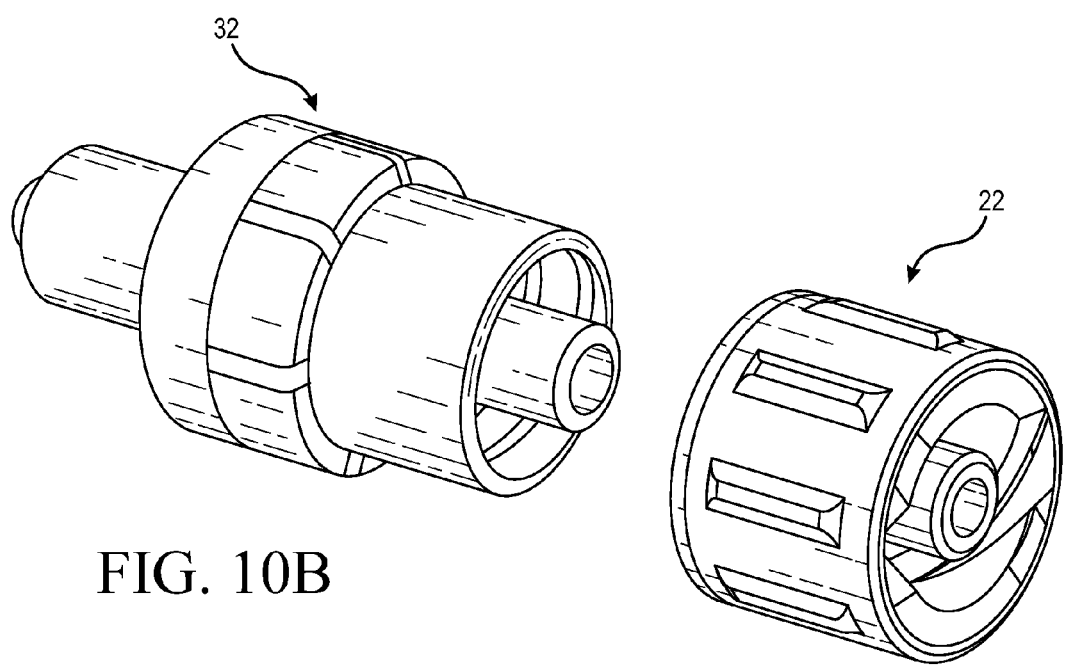
FIG. 10b shows the one-way flow valve being separated from the male connector of the instant invention.
Figure 10A:
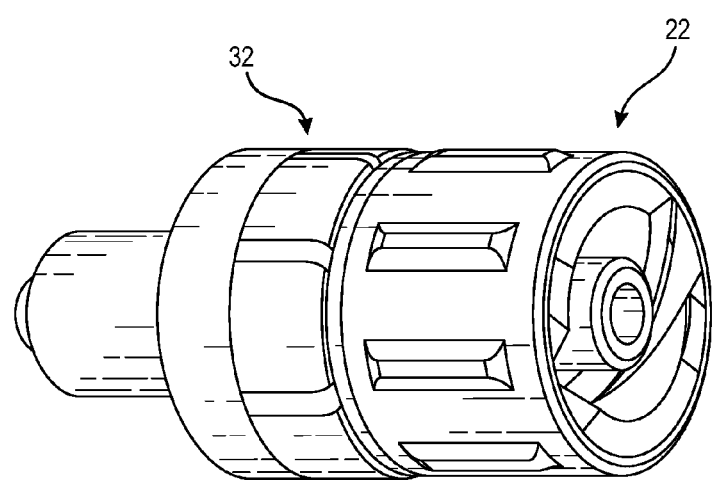
FIG. 10a is a male connector of the instant invention having integrated thereto a one-way flow valve.

FIG. 10A shows a male connector 22 of the instant invention having integrated or bonded thereto a one way flow valve 32, and FIG. 10B is an illustration of the inventive male connector 22 and the one way valve 32 being separate components. The one way flow valve 32 is used to prevent a fluid from flowing backwards, or back flow, from the outlet connector so as to ensure that the medicament only flows unidirectionally from the medicament store to the patient. There are two types of flow valves that may be used with the instant invention. An anti-syphon valve (ASV) may be integrated to the male connector 22 to prevent fluid from being sucked out of the male connector (by requiring a certain height differential), and a back check valve (BCV) may be integrated to the male connector 22 to prevent fluid from being sucked in though the male connector. Either way, but depending also on other parameters such as the difference in height between the fluid store and the connector which are not essential to the understanding of the instant invention, the use of one of those valves prevents the back flow of the fluid medicament back to the tubing. FIG. 10*a* shows an anti-syphon valve (ASV) integrally bonded or glued to a male connector 22, while FIG. 10*b* shows a back check valve (BCV) being separated from the male connector 22 prior to bonding. Both of the ASV and BCV valves are made by the Borla company of Italy.

FIGS. 11A-11B are the inside layout view and outside clam shell members view, respectively, of the clam shell tube retainer device 8 that retains the catheter 6 for insertion to the patient, per discussion above.

The various components of the first embodiment of the instant invention having now been described, with reference to FIG. 1, it can be seen that by coupling the appropriate pairs of inventive male/female connectors, a fluid through path is established from the fluid store bag 3*c* housed in cassette 3 through tubing 2, extension tubing 20, filter 14, tube retainer device 8 and finally to catheter 6 so that the medicament stored in bag 3*c* may be conveyed to the patient. Given that the flow of the medicament is controlled by the computerized ambulatory infusion pump, the flow and the amount of the flow of the medicament to the patient are regulated. Moreover, given that the male and female connectors of the instant invention can only be connected to each other as they are complementary configured, inadvertent coupling of those connectors to conventional connectors such as luer connectors that have a configuration that is not complementary to the given configuration of the inventive connectors are prevented, thereby averting potentially disastrous mishaps of potentially connecting a patient to the wrong medicament.

Figure 13:
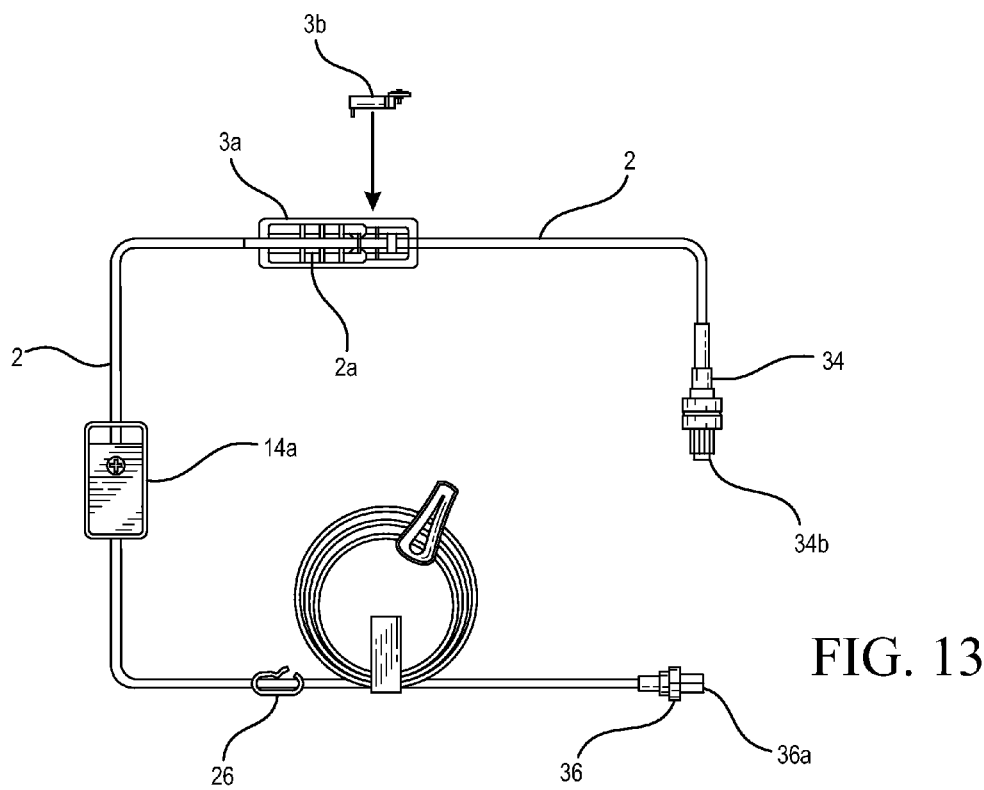
FIG. 13 is an illustration of the second embodiment of the instant invention that is similar to that show in FIG. 12 but relates to a high volume administration set.
Figure 12:
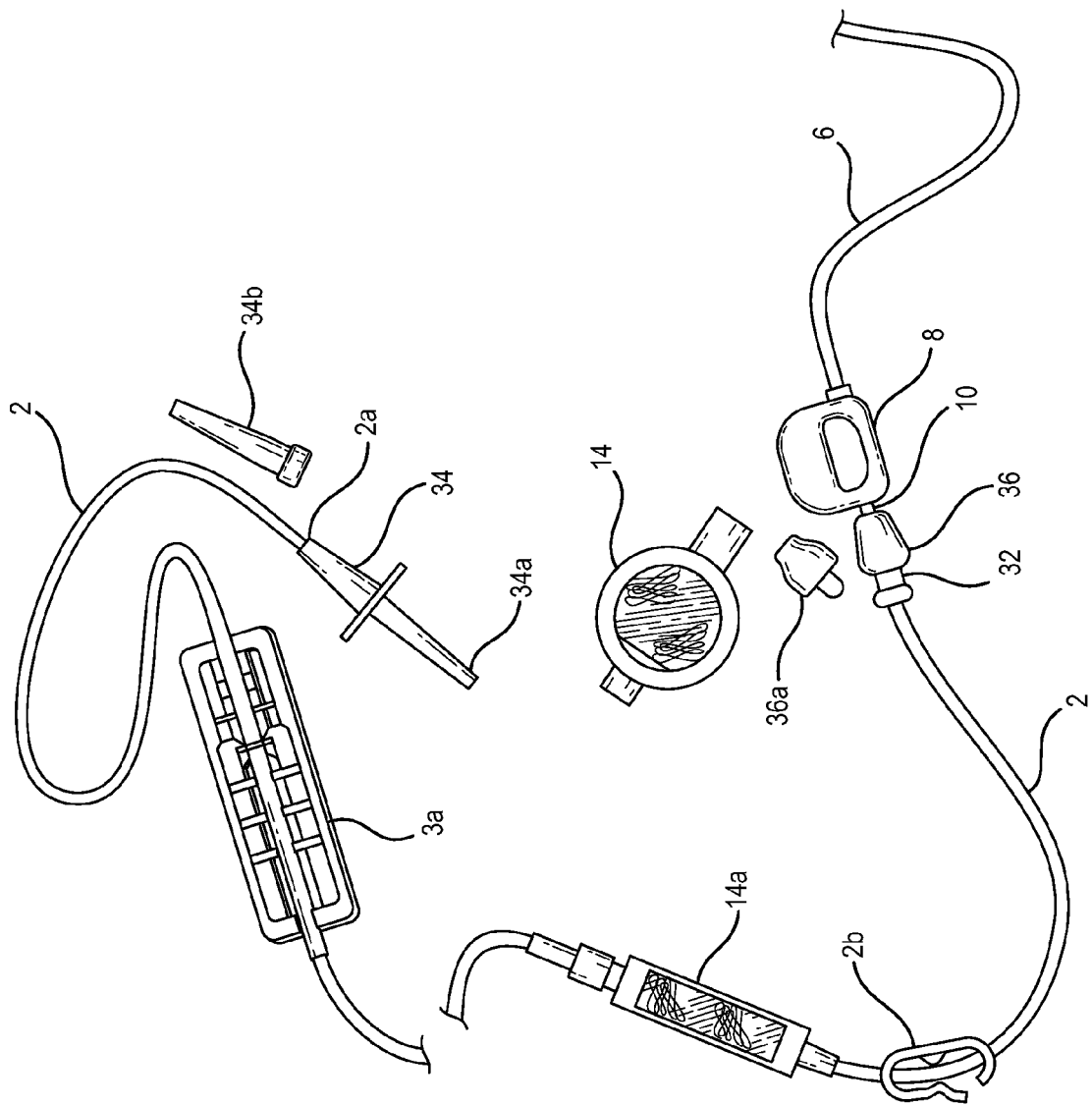
FIG. 12 is an overall view of a second embodiment of the instant invention that relates to a standard administration set.

A second embodiment of the instant invention, as shown in FIGS. 12 and 13, relates to administration sets that are used to convey medicaments from a fluid store to the patient. Elements or components that are the same as the first embodiment are designated the same in FIGS. 12 and 13. For the embodiment shown in FIG. 12, instead of a cassette that contains a fluid storage bag, tubing 2 has fitted to its inlet 2a a hollow spike 34 having a spike portion 34a that is used to pierce a conventional fluid store medicament bag (not shown), that may be adhesively attached to the patient or hung from a pole. Tubing 2 has a portion thereof positioned onto a mounting or press plate 3a that is couplable to a computerized ambulatory infusion pump such as that discussed above with respect to FIG. 2a, so that the flow and amount of the medicament through tubing 2 may be regulated. Tubing 2 may have a filter 14a bondedly integrated thereto for filtering out particulates that may be in the medicament. A clip 2b may be attached to tubing 2 to enable the user to crimp the tubing when needed. There is no extension tubing in the second embodiment, as the outlet of the tubing 2 has bondingly fitted thereto a male connector 36 having the same exemplar configuration as shown, for example in FIGS. 7a-7d. A one-way flow valve 32 is integrated to male connector 36 to prevent back flow of the medicament. Given that there is no extension tubing, male connector 36 is directly connected to the female connector 10 of tube retainer device 8, which securely but non-occludedly retains the catheter 6 which proximal end is inserted through the rubber tubing 8e (FIG. 11a) and which distal end is used to interface with a patient as described above. A cap 34b covers the sharp portion 34a of spike 34. Another cap 36a covers the mating portion of male connector 36. The filter 14 that interposes between retainer device 8 and male connector 36 in the FIG. 1 embodiment has been removed from the FIG. 12 embodiment, insofar as filter 14a is incorporated to tubing 2. The medicament conveying system of FIG. 12 may be referred to as a standard administration set that is adapted to convey a standard amount of medicament to the patient from the fluid store.

FIG. 13 shows a high volume administration set that functions the same as the administration set of FIG. 12 but for the amount of fluid flow that may be conveyed thereby. As its name implies, the high volume administration set of FIG. 13 is capable of conveying a higher volume of fluid medicament than the FIG. 12 administration set. Portion 2a of tubing 2 of the FIG. 13 administration set is mounted onto press plate 3a prior to press plate 3a being coupled to the infusion pump. The operation and the various components associated with plate 3a are the same as was discussed with respect to the FIG. 1 embodiment.

Figure 14:
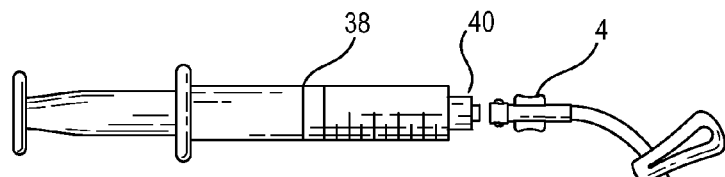
FIG. 14 shows a syringe with a specially configured connector that is matable to the specially configured counterpart connector for the tubing that extends to the fluid storage cassette of the instant invention system.

FIG. 14 shows a syringe 38 having an outlet connector 40 that is specially designed to have a configuration that is complementary to that of the CI connector 4 of the fluid storage cassette 3 of the drug delivery system of the instant invention. As discussed above, connector 4, which is bondedly connected to tubing 2, which in turn extends from the fluid storage or IV bag inside cassette 3, is a female connector that has a given configuration that prevents it from mating to a conventional male luer connector. For the FIG. 14 embodiment, syringe 38 is designed to have a male connector 40 that has a configuration complementary to that of connector 4, per illustrated in FIGS. 7a-7b, so that female connector 4 of the fluid storage cassette can be directly coupled to the male connector 40 of syringe 38. As a result, in the instance where bag 3c of the cassette 3 needs to be filled, the medicament in syringe 38 may be fed through the matingly coupled connectors 40 and 4 through tubing 2 into the fluid storage bag 3c inside cassette 3. The thus filled cassette may then be used with the ambulatory pump 30 of FIG. 2a to selectively provide the medicament to the patient, per discussed above.

Figure 15:
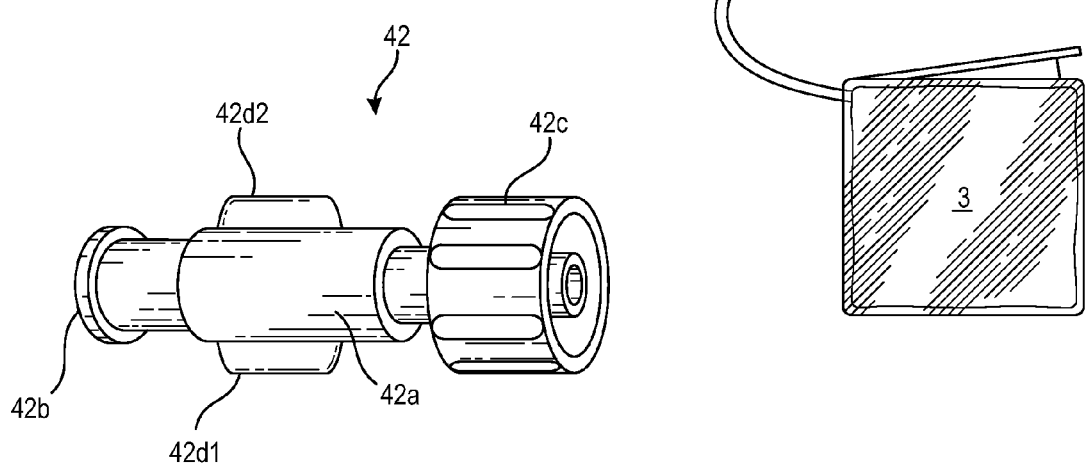
FIG. 15 shows an inventive fitting that is adaptable to act as a bridge to establish a fluid path between a connector of a conventional configuration and a counterpart connector of a given configuration that are not directly matable to each other.

FIG. 15 shows a filling adapter fitting or bridging connector 42 that is used to establish a connection between a connector that has a conventional configuration and a connector of the instant invention that has a given configuration. Fitting 42 may be a one-piece integral molded fitting, or may have the male connector with the given configuration bondedly attached to the female connector having the conventional configuration, or visa-versa. In detail, fitting 42 has a main body 42a having at its one end a female connector 42b, for example a conventional female luer connector, and at its other end a male connector 42c, for example a male connector of a particular given configuration that enables it to be matingly coupled to a complementary female connector of the same given configuration such as connector 4 shown in FIG. 1 but is not matable to a conventional female connector. For ease of discussion, connector 42b may be referred to as a first end connector and connector 42c may be referred to as a second end connector of fitting 42. The conventional female connector 42b may be matingly coupled to a counterpart male connector having a conventional configuration such as a male luer connector. Fins or wings 42d1 and 42d2 are provided at body 42a of fitting 42 to enable a user to more firmly grasp fitting 42, when coupling the fitting to counterpart connectors. A through passage extends longitudinally along the length of fitting 42 so that a fluid path may be established through fitting 42, when connectors 42b and 42c are matingly coupled to their respective counterpart connectors.

It should be noted that in place of the fitting of FIG. 15, the male connector 42c (CI connector) of the particular configuration and the luer female connector 42b of the conventional configuration may be bonded to a tubing such as 20 shown in FIG. 1 to effect a bridging extension set, for use in those instances where an extension tubing for establishing a connection between complementary conventional luer and CI connectors is needed.

Figure 7A:
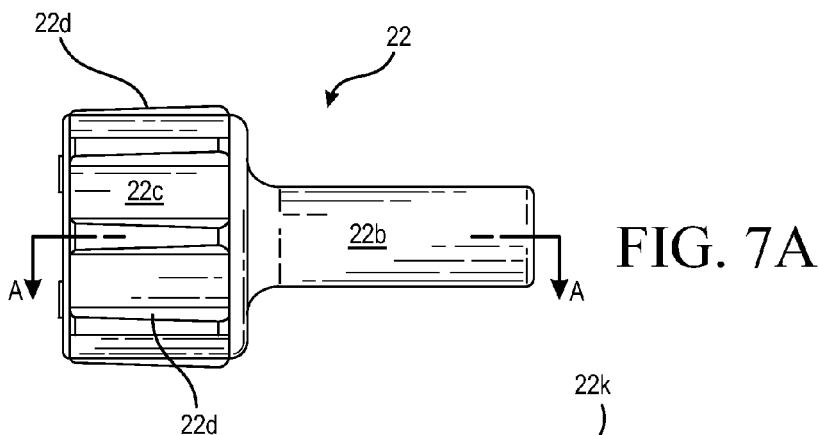
FIG. 7a is a side view of a male connector of the instant invention.
Figure 7B:
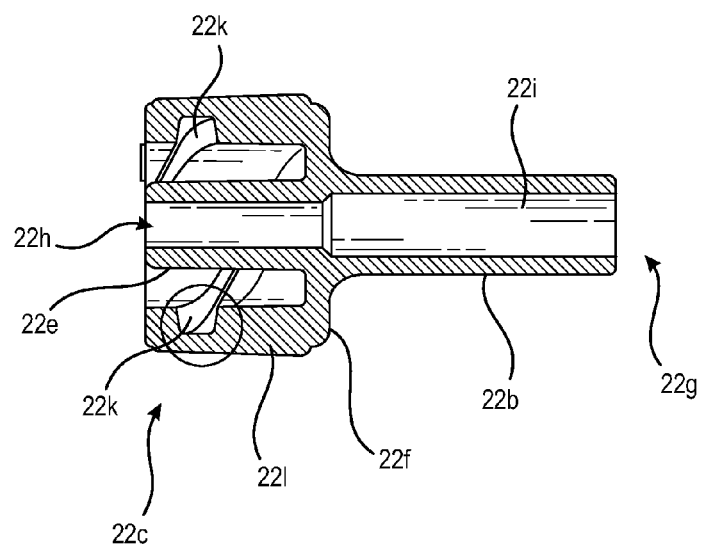
FIG. 7b is a cross-sectional view of the male connector of the instant invention as shown at section A-A of the FIG. 7a view.
Figure 7C:
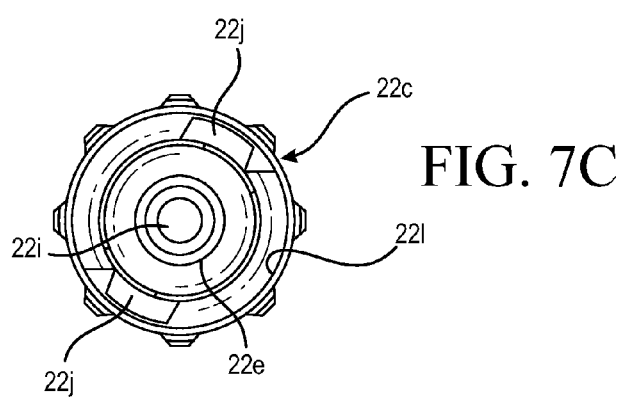
FIG. 7c is an end view of the male connector of the instant invention.
Figure 7D:
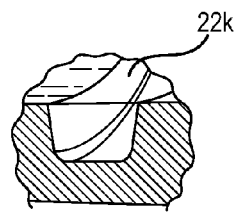
FIG. 7d is an enlarged view of the circled portion of the male connector per shown in FIG. 7b.

For the fitting shown in FIG. 15, the male CI connector has the same configuration as the male connector shown in FIGS. 7a and 7d, while connector 42b is a conventional female luer connector. Of course, the inventive fitting may in fact have a female connector that has the given configuration, i.e., a female CI connector, while its male connection may have a conventional configuration, i.e., a male luer connector. But for the embodiment shown in FIG. 15 and to be discussed for the remainder of the specification, fitting 42 is assumed to have a conventional female luer connector and a male connector of a given configuration that is not matable to a conventional female luer connector.

To provide the notice to the clinician that fitting 42 is a special connector for coupling connectors of different configurations for particular types of procedures, fitting 42 may be molded to have a particular color, for example orange, so that the clinician would know at a glance that the fitting is to be used as a bridging connector for connectors to be used with particular types of procedures, for example neuraxial anesthesia procedures (which may include spinal, epidural and caudal blocks), that require that connectors of a given configuration be used so that there is no mistake in connecting the tubing(s) required for the procedures with tubings that have conventional luer type connectors or connectors that have configurations different from the given configuration. The connectors of the given configuration (CI connectors) in turn may be molded or extruded to include a colorant such as for example yellow to signify that those connectors are for use with particular procedures, for example the neuraxial anesthesia procedures, and therefore have specially designed receptacle connector ends that prevent those connectors from being matingly coupled to counterpart conventional luer connectors.

Figure 16:
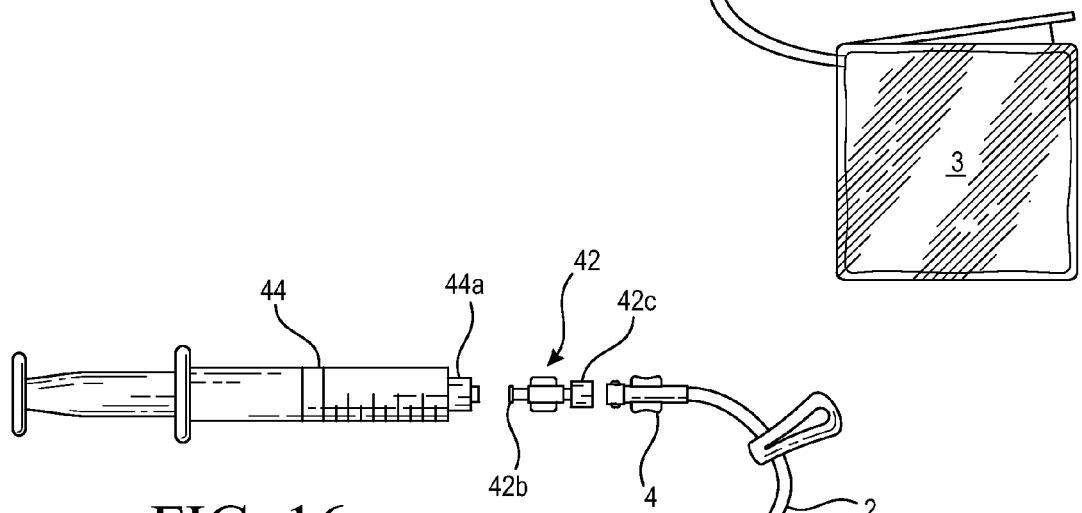
FIG. 16 shows the fitting of FIG. 15 being used to connect a conventional syringe to the fluid storage cassette of the instant invention system.

FIG. 16 shows the inventive fitting 42 being used as a bridge connector to connect a conventional syringe 44 having a conventional male luer connector 44a to the inventive connector 4 of the drug delivery system of the instant invention. As the fluid store represented by cassette 3 and connector 4 are the same as those components shown in FIG. 14, no further discussion is deemed to be necessary herein. The thing to note in FIG. 16 is the showing that the conventional female luer connector 42b of fitting 42 may be matingly coupled to the conventional male luer connector 44a of syringe 44, while the inventive CI male connector 42c of fitting 42 may be matingly coupled to the counterpart CI female connector 4 of the fluid storage cassette 3. Once the end connectors 42b and 42c of fitting 42 are matingly coupled to the respective connectors 44a of syringe 44 and connector 4 of cassette 3, a fluid path is established between syringe 44 and cassette 3, so that fluid may be conveyed between syringe 44 and cassette 3. For the embodiment shown, cassette 3 may be filled with the medicament in syringe 44, once a fluid path is established between syringe 44 and cassette 3 by fitting 42. Fitting 42 may therefore also be referred to as a filling fitting.

FIG. 17 shows fitting 42 being used to establish a fluid path between an IV bottle 46 that contains a medicament for filling cassette 3. Although IV bottle 46 is shown, it should be appreciated that IV bottle 46 in fact represents other fluid stores such as for example an IV bag. As shown, a conventional tubing set 48 has a hollow spike 48a is connected by means of a tubing 48b to a conventional male luer connector 48c. Spike 48a is inserted through a septum at the neck 46b of bottle 46, so that fluid stored in the bottle 46 may be conveyed to tubing 48b. As connector 48c is a conventional male luer connector, it is not matable to the counterpart inventive female connector 4 which has a configuration that is not complementary to that of connector 48c. By interposing fitting 42 between connectors 48c and 4, connector 48c is matingly coupled to the counterpart female luer connector 42b of fitting 42, while CI connector 4 is matingly coupled to the counterpart male CI connector 42c of fitting 42. Once the end connectors of fitting 42 are matingly coupled to their corresponding connectors, a fluid path is established between IV bottle 46 and cassette 3. As a result, the medicament in bottle 46 may be conveyed through tubing 48b, the through passage of fitting 42 and tubing 2 to fill the bag in cassette 3. When filled, cassette 3 may be used with the ambulatory pump as discussed above for selectively providing the medicament stored therein to the patient.

In addition to the tubing set 48 shown in FIG. 17, the inventive fitting 42 may also be used with other administration sets, such as those shown in FIGS. 12 and 13, of the drug delivery system of the instant invention.

It is the intension of the inventors that all matter described throughout this specification and shown in the accompanying drawings be interpreted as illustrative only and not in a limiting sense. Accordingly, it is intended that the invention be limited only by the spirit and scope of the hereto appended claims

The invention claimed is:

1. A drug delivery system, comprising:
a fluid store for storing a medicament;
a first tubing having an inlet in fluid communication with said fluid store so that the medicament flows from said fluid store through said first tubing, said first tubing having an outlet first connector of a given configuration that prevents said outlet first connector from mating with a counterpart connector having a conventional luer configuration;
a tube retainer device having an inlet second connector and an outlet whereinto a proximal end of a second tubing for interfacing with a patient is inserted, the second tubing having a distal end to be inserted to the patient and the inlet second connector having a configuration complementary to said given configuration of said outlet first connector so that said inlet second connector is connectable only to said outlet first connector and not to a counterpart connector having a conventional luer configuration, the tube retainer device having an open position wherein the second tubing is removable from the tube retainer device and a closed position wherein the second tubing is fixedly held by the tube retainer device to establish a fluid communication path with the inlet second connector; and
a one way flow valve integrated to said outlet first connector to prevent back flow of the medicament from said second tubing to said first tubing to ensure that the medicament flows unidirectionally from said first tubing to said second tubing;
wherein a fluid through path is established for the medicament to flow from said fluid store to said second tubing through said first tubing when said outlet first connector and said inlet second connector of complementary given configurations are connected to each other.

2. A drug delivery system of claim 1, wherein said outlet first connector comprises a male connector having said given configuration and said inlet second connector comprises a female connector having a configuration complementary to said given configuration.

3. A delivery system of claim 1, wherein the inlet of said first tubing comprises a hollow spike that is inserted to said fluid store to establish a fluid path between said fluid store and said first tubing.

4. A drug delivery system of claim 1, further comprising a mount whereonto a portion of said first tubing is positioned, said mount being coupled to a computerized controlled pump having a flow control mechanism that interacts with the portion of said first tubing positioned onto the mount to selectively occlude and open said first tubing to control the flow of the medicament through said first tubing to thereby regulate the amount of medicament to be dispensed to the patient.

5. A drug delivery system of claim 1, wherein said tube retainer device comprises a clam shaped structure having two clam members that are pivotally closeable upon each other, and wherein said inlet second connector extends from one of said clam members; and
wherein said second tubing comprises a catheter having the proximal end that connects to and extends from an inlet of said clam shaped structure to establish the fluid communication with the inlet second connector and the distal end to be inserted to the patient, a proximal portion of the catheter being positioned between said clam members so as to be fixedly grasped by said clam members when said clam members close upon each other, the catheter establishing a through path for the medicament to flow from said fluid store to the patient.

6. A drug delivery system of claim 1, further comprising a filter bondedly integrated to said first tubing to at least trap unwanted particulates from the medicament flowing through said first tubing.

7. A drug delivery system comprising:
a fluid store for storing a medicament;
a first tubing having an inlet in fluid communication connection with said fluid store so that the medicament flows from said fluid store through said first tubing, said first tubing having an outlet first connector of a given configuration that prevents said outlet first connector from connecting with a counterpart connector of a conventional luer configuration;

a tube retainer device having an inlet second connector and an outlet whereinto a first end of a second tubing for interfacing with a patient is inserted, the inlet second connector having the same said given configuration as said outlet first connector of said first tubing so that said inlet second connector is not connectable with a counterpart connector of a conventional luer configuration, the second tubing including another end to be inserted to the patient, the tube retainer device having an open position wherein the second tubing is removable from the tube retainer device and a closed position wherein the second tubing is fixedly held by the tube retainer device to establish a fluid communication path with the inlet second connector; and an extension tubing having a first end fitted with a third connector and a second end fitted with a fourth connector, said third and fourth connecters each having a configuration complementary to said given configuration so that said third connector is connectable with said first connector but not with a counterpart connector of a conventional luer configuration and said fourth connector is connectable with said second connector but not with a counterpart connector of a conventional luer configuration, said extension tubing connected to said first tubing via the coupling of said first and third connectors and to said tube retainer device via the coupling of said second and fourth connectors to establish a fluid through path from said fluid store to said second tubing.

8. A drug delivery system of claim 7, further comprising a one way valve integrated to said first connector to prevent back flow of the medicament from said extension tubing to said first tubing.

9. A drug delivery system of claim 7, further comprising a one way valve integrated to said fourth connector to prevent back flow of the medicament from said second tubing to said extension tubing.

10. A drug delivery system of claim 7, wherein said fluid store comprises a cassette having a mount whereonto a portion of said first tubing is positioned, said mount being coupled to a computerized controlled pump having a flow control mechanism that interacts with the portion of said first tubing positioned on the mount to selectively occlude and open said first tubing to control the flow of the medicament through said first tubing to thereby regulate the amount of medicament to flow to said second tubing.

11. A drug delivery system of claim 7, wherein said first connector of said first tubing may be disconnected from said third connector of said extension tubing and be connected to a syringe with a conventional connector having a configuration complementary to said given configuration.

12. A drug delivery system of claim 7, wherein said tube retainer device comprises a clam shaped structure having two clam members that are pivotally closeable upon each other, and wherein said second connector extends from one of said clam members; and wherein said second tubing comprises a catheter having the proximal end that connects to and extends from an inlet of said clam shaped structure to establish the fluid communication with the inlet second connector and the another end to be inserted to the patient, a proximal portion of the catheter being positioned between said clam members so as to be fixedly grasped by said clam members when said clam members close upon each other, the catheter establishing a through path for the medicament to flow from said fluid store to the patient.

13. A drug delivery system of claim 7, wherein said first connector and said second connector each comprise a female connector having said given configuration, and said third and fourth connectors each comprise a male connector having a configuration complementary to said given configuration.

14. A drug delivery system of claim 7, wherein said tube retainer device has a catheter for insertion to the patient, said tube retainer device including an inlet female connector having said given configuration, said system further comprising:

a filter having an inlet female connector of said given configuration for mating with said fourth connector and an outlet male connector having a configuration complementary to said given configuration;

wherein said female connector at the inlet of said tube retainer device and said outlet male connector of said filter are complementary coupled to each other to establish a fluid path between said extension tubing and the catheter of said tube retainer device via said filter.

15. A drug delivery system, comprising:

a fluid store for storing a medicament;

a first tubing having an inlet in fluid communication connection with said fluid store so that the medicament flows from said fluid store through said first tubing, said first tubing having an outlet female connector of a given configuration that prevents it from mating to a counterpart male connector of a conventional luer configuration;

a tube retainer device having a catheter for insertion to a patient including an inlet female connector having the same said given configuration as the outlet female connector of said first tubing, the inlet female connector of said tube retainer device not matable to a male connector of the conventional luer configuration, the tube retainer device having an open position wherein the catheter is movable from the tube retainer device and a closed position wherein the catheter is fixedly held by the tube retainer device to establish a fluid communication path with the inlet female connector;

an extension tubing having a first end male connector and a second end male connector each having a configuration complementary to said given configuration so that said first end male connector is matable to the outlet female connector of said first tubing but not to a female connector of a conventional luer configuration and said second end male connector is matable to the inlet female connector of said tube retainer device but not to a female connector of a conventional luer configuration;

wherein a fluid through path from said fluid store to said catheter is established when said extension tubing is coupled to said second tubing via the mating of its first end male connector with the outlet female connector of said first tubing and the mating of its second end male connector with the inlet female connector of said tube retainer device.

16. A drug delivery system of claim 15, further comprising:

a one way valve integrated to the second end male connector of said extension tubing that mates with the inlet female connector of said tube retainer device to prevent back flow of the medicament from said catheter to said extension tubing.

17. A drug delivery system of claim 15, wherein said fluid store comprises a cassette having a mount whereonto a portion of said first tubing is positioned, said mount being coupled to a computerized controlled pump having a flow control mechanism that interacts with the portion of said first tubing to selectively occlude and open said first tubing to control the flow of the medicament through said first tubing to thereby regulate the amount of medicament to flow to said catheter.

18. A drug delivery system of claim 15, wherein said tube retainer device comprises a clam shaped structure having two clam members that are pivotally closeable upon each other from the open position, and wherein said second end male connector extends from one of said clam members; and wherein said catheter has a proximal end that connects to and extends from an inlet of said clam shaped structure and a distal end to be inserted to the patient, a proximal portion of the catheter being positioned between said clam members so as to be fixedly grasped by said clam members when said clam members close upon each other in the closed position, the catheter establishing a through path for the medicament to flow from said fluid store to the patient.

19. A drug delivery system, comprising:

a fluid store for storing a medicament;

a first tubing having an inlet in fluid communication with said fluid store so that the medicament flows from said fluid store through said first tubing, said first tubing having an outlet male connector of a given configuration that prevents it from mating with a female connector of a conventional luer configuration;

a tube retainer device having a second tubing coupled thereto for insertion to a patient including an inlet female connector having a complementary configuration to said given configuration of said outlet male connector of said first tubing so that said inlet female connector is connectable only to said outlet male connector of said given configuration and not to a male connector of a conventional luer configuration to establish a through path for the medicament to flow from said fluid store to the patient through said first and second tubings when said outlet male connector and inlet female connector of complementary given configurations are connected to each other, the tube retainer device having an open position wherein the second tubing is removable from the tube retainer device and a closed position wherein the second tubing is fixedly held by the tube retainer device to establish a fluid communication path with the inlet female connector; and a mount whereonto a portion of said first tubing is positioned, said mount being coupled to a computerized controlled pump having a flow control mechanism that interacts with the portion of said first tubing positioned on said mount to selectively occlude and open said first tubing to control the flow of the medicament through said first tubing to thereby regulate the amount of medicament dispensed to the patient.

20. A drug delivery system of claim 19, further comprising a one way flow valve integrated to said outlet male connector to prevent back flow of the medicament from said second tubing to said first tubing.

* * * * *